United States Patent [19]

Poignant et al.

[11] 4,013,451
[45] Mar. 22, 1977

[54] HERBICIDAL COMPOSITIONS FOR KILLING WEEDS IN VINEYARDS

[75] Inventors: Pierre Poignant; Guy Borrod; Raymond Richard, all of Lyon, France

[73] Assignee: Philagro S.A., Lyon, France

[22] Filed: Sept. 5, 1975

[21] Appl. No.: 610,865

[30] Foreign Application Priority Data

Sept. 20, 1974 France .............................. 74.32560

[52] U.S. Cl. .................................. 71/116; 71/108; 71/118
[51] Int. Cl.² .......................................... A01N 9/24
[58] Field of Search ............................. 71/116, 108

[56] References Cited
UNITED STATES PATENTS 2,957,760   10/1960   Tarfuro et al. ...................... 71/116

FOREIGN PATENTS OR APPLICATIONS 1,318,847   0000   France

OTHER PUBLICATIONS

Lhoste "Les desherbants chimiques" p. 113 (1965).
Kaufhold "Control of Weeds in Vineyards with Hormone-like Herbicides" Chem. Abst. vol. 6H (1966) 13320c.

*Primary Examiner*—Lewis Gotts
*Assistant Examiner*—Catherine L. Mills
*Attorney, Agent, or Firm*—Browdy and Neimark

[57] ABSTRACT

A composition for selective weed control in vineyards and orchards containing as active material at least one of the following compounds:

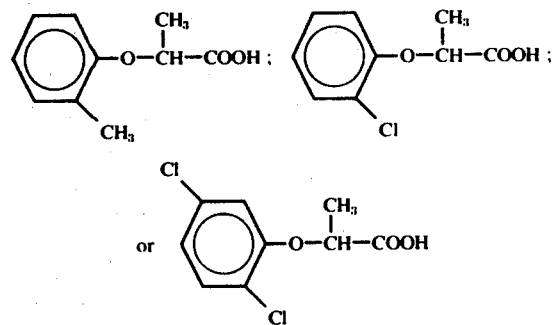

10 Claims, No Drawings

HERBICIDAL COMPOSITIONS FOR KILLING WEEDS IN VINEYARDS

FIELD OF THE INVENTION

This invention relates to compositions intended for selective weed control in vineyards and orchards. More particularly, the invention relates to compositions intended for controlling dicotyledons, more especially perennial dicotyledons such as bindweed. Finally, the invention relates to a method of controlling the weeds, more especially bindweeds, which overrun vineyards and orchards.

The compositions according to the invention contain, as active material, at least one phenoxy propionic acid corresponding to the formula

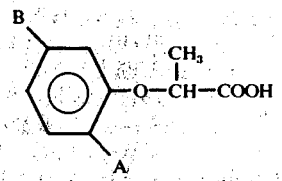

in which
A = $CH_3$ or Cl,
B = H where A represents $CH_3$, or = H or Cl where A represents Cl.

Accordingly, there are three active materials of the kind in question, namely:

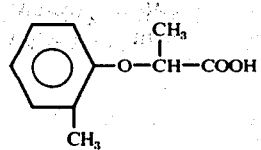

or (2-methylphenoxy)-2-propionic acid hereinafter referred to in short as MPP,

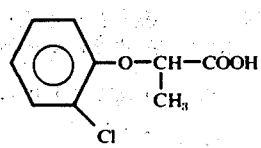

or (2-chlorophenoxy)-2-propionic acid which will hereinafter be referred to in short as CPP, and

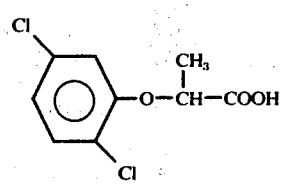

or (2,5-dichlorophenoxy)-2-propionic acid which will hereinafter be referred to in short as DPP.

BACKGROUND OF THE INVENTION

The problem of controlling perennial dicotyledons, more especially bindweeds, in orchards and above all in vineyards is becoming increasingly more important every year in the major tree-growing and vine-growing countries. Ever-increasing labor costs are making it more and more difficult to carry out weed control by agricultural methods, and tree growers or vine growers expect the chemical industry to provide them with the herbicidal means required for effective weed control in their vineyards and orchards.

Although a certain number of products have already been proposed, none of them has produced really satisfactory results in efforts to control the bindweeds: field bindweed (*Convolvulus arvensis*) and bearbine (*Calysthegia sepium*), which are two of the most troublesome weeds, especially in vineyards. These weeds are able to develop extremely long shoots which twine themselves around vine stocks and, subsequently, around the vine shoots and clusters. These bindweeds cause very serious damage to the vine both by robbing them of nutritional elements present in the soil and by purely mechanical action during harvesting, resulting in the loss of numerous clusters which are "stripped" of their grapes when the vine harvester gathers the cluster.

It is known that compounds belonging to the phenoxyalkane carboxylic acid family, or phytohormones, have a very good destructive effect upon bindweed. By acting through a hormonal mechanism, they migrate into the shoots of the bindweed which are deformed and then die. Unfortunately, these phytohormones are also well known for their extremely phytotoxic effect on the vine which, when brought into contact with extremely small quantities of these phytohormones, undergoes characteristic and often irreversible deformation.

The dangers of using these compounds have been repeatedly emphasized, more especially during the 6th Conference of Columa (Cannes, 8th-10th December 1971). Various authors specializing in problems of this kind have been prompted to make remarks such as "the use of 2,4-D in vine-growing would still appear to be tricky and hazardous: its effectiveness on bindweed is undoubtedly satisfactory . . . but the dangers of phytotoxicity on leaves or clusters are so great that it would be dangerous to popularize its use" (Barralis et al.: Report of the 6th Columa, page 703), and even "2,4-D . . . remains the most effective and least onerous formulation. it is also one of the most difficult to use . . . " (Agulhon et al.: Report of the 6th Columa, page 745).

This type of remark under the signature of specialists in viticulture clearly underlines the fact that it is almost impossible to use 2,4-D in arboriculture and viticulture. In addition, this type of application is not recommended by any company because the risks involved are too great.

The same phenomena and the same disadvantages are encountered in the use of compounds related to 2,4-D, such as 2,4-DP (2,4-dichlorophenoxy propionic acid) and MCPP (2-methyl-4-dhlorophenoxy propionic acid), which, despite their indisputable action on bindweed, are no longer used for the same reason.

The acids MPP, CPP and DPP are known products: the first two are described in particular in French Patent 1,313,847 (Boots) as selective herbicides for cereal crops and clover. The acid MPP is also described in the work by J. Lhoste "Les desherbants chimiques" (page 113), 1965, in which the following conclusion is reached on this compound: "It would not seem that satisfactory results can be expected from this compound".

SUMMARY OF THE INVENTION

It has now been found, all the more surprisingly in the light of the prior art discussed above, that specific derivatives of the phenoxyalkane carboxylic acid family have a very powerful herbicidal effect on bindweed without any of the disadvantages, with respect to the vine, of 2,4-D and its homologs.

Even more surprisingly, the effect of the compounds according to the invention is developed through a herbicidal action mechanism vastly different from conventional phytohormones because the bindweeds are destroyed through a mechanism which does not cause deformation of the hormonal type, and because none of the previously known classic phytotoxic symptoms has been observed, even in vines.

It is, accordingly, an object of the invention to overcome the defects in the prior art, such as indicated above; it is another object to provide for selective weed control in vineyards and orchards; it is another object to provide improved control against dicots such as bindweed without phytotoxic effect against trees and grape vines.

DESCRIPTION OF THE PREFERRED EMBODIMENTS

Accordingly, the compounds according to the invention correspond to the general formula:

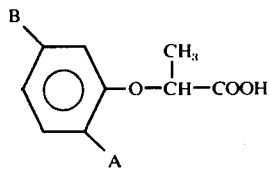

(1)

in which A and B are as defined above.

Simple derivatives of the acids MPP, CPP and defined above may also be used in accordance with the invention.

In the context of the invention, simple derivatives of these acids are their metal salts, such as their sodium, potassium, ammonium salts or the salts of heavier metals obtained by condensing the acid with the corresponding metallic hydroxide;

their water-soluble or fat-soluble amine or alkanolamine salts obtained by condensing the acid with primary, secondary or tertiary amines, such as methylamine, ethylamine, diethylamine, isopropylamine, trimethylamine, cyclohexylamine, or with monohydroxylated or polyhydroxylated alkanolamines, such as monoethanolamine, diethanolamine, triethanolamine, etc.

their esters and more especially their alkyl esters, such as methyl, ethyl, isopropyl, isooctyl and cyclohexyl esters, their alkoxyalkyl esters, such as their butoxy ethanol esters, etc.

their unsubstituted amides.

These various forms of the acids according to the invention are generally characterized by similar herbicidal activities, but show different physicochemical characteristics (solubility, vapor pressure, etc.) which may make one or the other of these forms preferable for a particular application, depending upon the conditions under which it is to be used, for example.

The herbicidal properties of the compounds according to the invention were demonstrated in tests carried out under glass and then in the open, which showed both the wide range of herbicidal activity of the compounds according to the invention and also the complete absence of phytotoxicity on the vine.

Tests under glass

10 × 10 × 15 cm containers are filled with clean soil which had not previously been subjected to any herbicidal treatment. Seeds of various types of vegetables, whose sensitivity to the herbicidal product to be tested it is desired to study, are then placed on the soil. The seeds are then covered with a layer of earth in a thickness governed by the diameter of the seeds. In the case of bindweed, 5 bindweed plants with from 2 to 5 fully developed leaves are directly transplated in the containers, these plants having been previously grown in pots. Three weeks after transplanting in the case of the bindweed, or after germination and the formation of proper leaves in the case of the plants grown from seed, the containers are sprayed with the herbicidal composition to be tested. The herbicidal composition to be tested is in the form of a wettable powder prepared by mixing the following ingredients for 1 minute in a blade mill:

| | |
|---|---|
| active material to be tested | 20 % |
| deflocculant (calcium lignosulphate) | 5 % |
| wetting agent (sodium alkylaryl sulphonate) | 1% |
| filler (alumina silicate) | 74 % |

This wettable powder is then mixed with a quantity of water calculated for spraying in the required dose per hectare.

In each test, one control plant is left untreated in order to be able to determine any inhibition of growth and also to detect any absence of germination or defective growth of the plants due to particular conditions.

The containers thus treated are then kept under glass for a certain period under constant conditions of humidity, temperature and lighting. After 5 weeks, the results are assessed, in particular by evaluating the percentage destruction of each of the species in relation to the control.

The results obtained are set out in the following Table:

| Product | Doses kg/ha | % destruction of weeds | | | | |
|---|---|---|---|---|---|---|
| | | amaranth | chenopodium | mustard | stellaria | bindweed |
| MPP | 2 | 55 | 60 | 65 | 95 | 90 |
| | 4 | 90 | 90 | 80 | 100 | 100 |
| CPP | 2 | 95 | 100 | 60 | 95 | 100 |
| | 4 | 100 | 100 | 85 | 100 | 100 |
| DPP | 2 | 40 | 85 | 40 | 100 | 100 |

-continued

| Product | Doses kg/ha | % destruction of weeds | | | | |
|---|---|---|---|---|---|---|
| | | amaranth | chenopodium | mustard | stellaria | bindweed |
| | 4 | 90 | 100 | 85 | 100 | 100 |

The high activity of these compounds, especially on bindweed, was by no means foreseeable and was all the more surprising insofar as related compounds such as 3,4-dimethylphenoxy acetic acid
4-isopropylphenoxy acetic acid
4-ethylphenoxy acetic acid
2-chloro-4-isopropylphenoxy acetic acid
4-tert.-butylphenoxy acetic acid and the beta-phenoxypropionic homologs of these compounds are inactive against bindweed, even in a dose of as large as 4 kg/ha. Accordingly, this activity is by no means attributable to the mere presence of a phenoxy acetic or phenoxy propionic group, but rather to preferential positions of certain substituents such as those which our research has revealed and which the present invention seeks to protect.

Open-air tests

The open-air tests were carried out in the Beaujolais region on 20 square meter plots of vines (Gamay variety) heavily overrun with field bindweed (*Convolvulus arvensis*). Before the treatment, the bindweed shoots measured 10 to 30 cm.

The various compounds used were used in the following forms:

| | |
|---|---|
| - MPP: | potassium salt |
| | monomethylamine salt |
| - CPP: | acid |
| | butyl glycol ester |
| | amide |
| - DPP: | sodium salt |
| | diethanolamine salt |
| | isooctyl ester. |

The treatment was carried out on the 7th June.

The results set out in the following Table correspond to averages of the results obtained with the various forms of active material.

| Product | Doses kg/ha | % destruction of bindweed on | |
|---|---|---|---|
| | | 8th July | 30th August |
| CPP | 2 | 75 | 90 |
| | 3 | 85 | 95 |
| DPP | 2 | 75 | 85 |
| | 3 | 90 | 95 |
| MPP | 2 | 85 | 90 |
| | 3 | 90 | 100 |

In these same tests, two commercial products based on 2,4-dichlorophenoxy acetic acid and 2,4-dichlorophenoxy propionic acid, in the form of their potassium salts, were used for comparison in the same doses and under the same spraying conditions.

The percentage destructions of the weeds present, especially bindweed, were of the same order as those obtained with the compounds according to the invention. On the other hand, these two compounds were found to have produced very distinct deformation of the hormonal type in the vine plants, which is characteristic of those compounds.

To the contrary, no manifestation of phytotoxicity or of the hormonal type or indeed of any other type was observed with the compounds according to the invention.

Since the conditions of treatment and the doses were the same, these differences in behavior with respect to the vine are entirely surprising in view of the large similarity existing between the chemical structures of the tested products and the reference products.

The doses in which the compounds according to the invention are used may vary within certain limits, depending in particular upon the type of soil, upon the conditions of treatment and upon the virulence of the weeds before the treatment. In general, doses of active material of from 1 to 6 kg/ha are sufficient, the preferred doses being from 2 to 4 kg/ha.

For their practical application, the compounds according to the invention are generally formulated by the methods commonly used in the herbicide industry. The object of formulating the active materials is to provide the user with compositions which are easy to use and whose activity on the plants is maximal. To this end, a certain number of fillers and various additives, depending upon the type of formulation envisaged and upon the desired result, are generally added to the pure active materials. Also, more than one active compound may be used in any given formulation.

These formulations are made up either in liquid form (emulsions, true solutions, pastes, suspensions, etc.) which are ready for use or which have to be diluted with water, or in the form of solids (wettable powders, granulates, etc.) which may be used as such or which have to be diluted in a liquid medium before use. Accordingly, these compositions comprise generally inert fillers and/or organic, mineral or mixed solvents and/or emulsifiers, adhesives, antilumping agents, deflocculants, etc.

Particulars of these formulations may be found in particular in the work by Fryer and Evans: Weed Control Handbook, 5th edition, pp. 101 et seq.

The additives preferably used in the formulations according to the invention include certain emulsifying products or surfactants which have been found in tests to reinforce the herbicidal activity of the compounds according to the invention to a considerable extent by a phenomenon of synergy which was unforeseeable in view of the fact that these same compounds have no herbicidal effect on their own. Preferred surfactants include ethoxylated alkyl phenols and, in particular, ethoxylated heptyl and nonyl phenols containing from 10 to 50 ethylene oxide units in their molecules, metallic alkyl sulphosuccinates and, in particular, sodium heptyl sulphosuccinates, or mixtures of these compounds.

It will be obvious to those skilled in the art that various changes may be made without departing from the scope of the invention and the invention is not to be considered limited to what is described in the specification.

What is claimed is:

1. A method of killing dicotyledon weeds in vineyards, comprising contacting said weeds with a quantity sufficient to kill said weeds of at least one compound of the formula

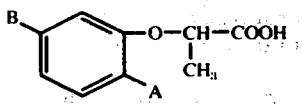

wherein A is $CH_3$ or Cl; B is H where A is $CH_3$ or B is H or Cl where A is Cl, or a simple derivative thereof.

2. A method as claimed in claim 1, wherein the weeds present are essentially of the bindweed type.

3. A method in accordance with claim 1, wherein said quantity is 1 – 6 kg/ha.

4. A method in accordance with claim 2 wherein said quantity is 2 – 4 kg/ha.

5. A process in accordance with claim 1, wherein said compound is mixed with an inert carrier and a surfactant.

6. A process in accordance with claim 1, wherein the active material is (2-methylphenoxy)-2-propionic acid corresponding to the formula

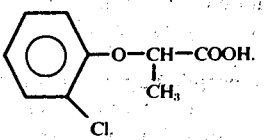

7. A process in accordance with claim 1, wherein the active material is (2-chlorophenoxy)-2-propionic acid corresponding to the formula

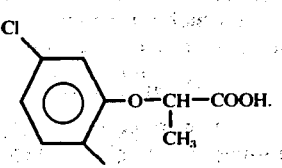

8. A process in accordance with claim 1, wherein the active material is (2,5-dichlorophenoxy)-2-propionic acid corresponding to the formula 9. A process in accordance with claim 5, wherein said surfactant is an ethoxylated alkyl phenol.

10. A process in accordance with claim 5, wherein said surfactant is a metallic alkyl sulphonate.

* * * * *